United States Patent [19]

Winner

[11] Patent Number: Plant 6,593

[45] Date of Patent: Feb. 7, 1989

[54] VARIETY OF GERANIUM NAMED MANDARIN

[75] Inventor: Blair L. Winner, Lompoc, Calif.

[73] Assignee: Denholm Seeds, Lompoc, Calif.

[21] Appl. No.: 73,807

[22] Filed: Jul. 15, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Ziesenheim & Webb

[57] ABSTRACT

A new geranium cultivar is distinguished by its clarity and intensity of the orange flower colors. The plant is compact, free flowering and has outstanding bloom production.

1 Drawing Sheet

BACKGROUND OF THE NEW PLANT

The present invention comprises a new and distinct cultivar of *Pelargonium hortorum* which is a zonal geranium known by the varietal name Mandarin. The new variety (Oglevee No. 88, Denholm No. 54650) was discovered in a selective breeding program by Mr. Blair L. Winner. The variety was derived from the F5 generation of a cross of Dandoratglut×F1 pink. This variety differs from Dandoratglut in flower color with the new variety having an intense orange color while Dandoratglut has an orange-scarlet color.

The new cultivar was discovered in April of 1983 at Denholm Seeds in Lompoc, Calif., was first asexually reproduced by cuttings by Denholm Seeds at Lompoc, Calif., and has been repeatedly asexually reproduced by cuttings at Oglevee Associates, Inc. in Connellsville, Pa. over a 36 month period. It has also been trail and field tested at Connellsville, Pa. yearly since the spring of 1984. It has been found to retain its distinctive characteristics through successive propagations.

The new cultivar, when grown in a glass greenhouse in Connellsville, Pa. using natural light, 65° F. day temperature, 58° F. night temperature and grown in a soilless media with constant fertilizer of 275–300 parts per million nitrogen and potassium, and 16 hours of high pressure sodium light has a response time from a rooted cutting to a flowering plant in a 10 cm pot of six weeks.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the cultivar. The data which define these characteristics were collected from asexual reproductions carried out by Oglevee Associates, Inc. in Connellsville, Pa. The plant histories were taken on plants blossomed under natural light under 200–220 foot candles of cool, white fluorescent light. Color references are primarily to the R.H.S. Colour Chart of The Royal Horticultural Society of London.

THE PLANT

Classification:

*Botanical.*—*Pelargonium*×*hortorum.*

*Commercial.*—Zonal geranium.

Form: Semi-dwarf; compact growth; free basal branching; flowers close to foliage; free and early flowering.

Height: 20.0–31.0 cm from media surface.

Growth: Free branching from base; compact growth; short internodes.

Strength: Stands upright without artificial support.

Foliage: Stalked leaf attachment; no zoning.

Leaves:

*Size.*—8.0–12.0 cm across.

*Shape.*—Reniform; Cordate Base.

*Margin.*—Crenate.

*Texture.*—Pubescent; Dull (Not reflective).

*Color.*—Top: Green group 137A. Bottom: Green group 138B.

*Ribs and veins.*—Palmate; Yellow-green 145B.

Petioles: Yellow-green group 144A; 6.0–9.0 cm in length.

Stem:

*Color.*—Yellow group 144B.

*Internodes.*—1.5–3.0 cm in length.

The bud:

*Shape.*—Upright; hemispherical cluster.

Size: 2.0–3.0 cm across.

INFLORESCENCE

Tonality from a distance: Orange.

Blooming habit: Continuous; upright; hemispherical in shape.

Size: 8.0–11.0 cm across.

Borne: Umbel; 3.0–6.0 cm above foliage; florets on pedicel; pedicel on peduncle.

Florets:

*Form.*—Flat to slightly cupped; round to ovate.

*Color.*—Top: Orange-red group 33A. Bottom: Orange-red group 32A.

*Petals.*—5 pedals per floret; separated — not united; margin entire; palmate veination; obovate; veins insignificant.

*Size.*—1.5–3.0 cm across.

*Texture and appearance.*—Smooth, pubescent, reflective.

Petaloids:

*Quantity.*—None observed.

Pedicel:

*Length.*—2.0–3.0 cm in length; Color: Greyed-orange group 174B.

Peduncle: Yellow-green group 144A; arises from node opposite leaf petiole; 15.0–17.0 cm in length.

REPRODUCTIVE ORGANS

Stamens:

*Anthers.*—Reddish-purple.

*Filaments.*—White at base to purple-red at tip; irregular in shape; flat; 0.3–0.7 cm in length.

*Pollen.*—Golden-yellow initially.

Pistils:

*Number.*—1 with 5 parted stigma.

*Length.*—7.0–8.0 mm.

*Stigma.*—1; 5 parted at maturity; Red-purple in color; 2.0 mm in length.

*Style.*—1; 2.0 mm in length; Red-purple in color.

Ovaries: 5.0 mm in length; 2.0 mm across; pale green-yellow in color; very pubescent (0.1 to 0.5 mm in length); superior.

Fruit: None observed.

The new cultivar is characterized by the clarity and intensity of the orange flower color. The plant is compact, free flowering and has outstanding bloom production.

I claim:

1. A new and distinct variety of geranium plant substantially as herein shown and described and parts thereof.

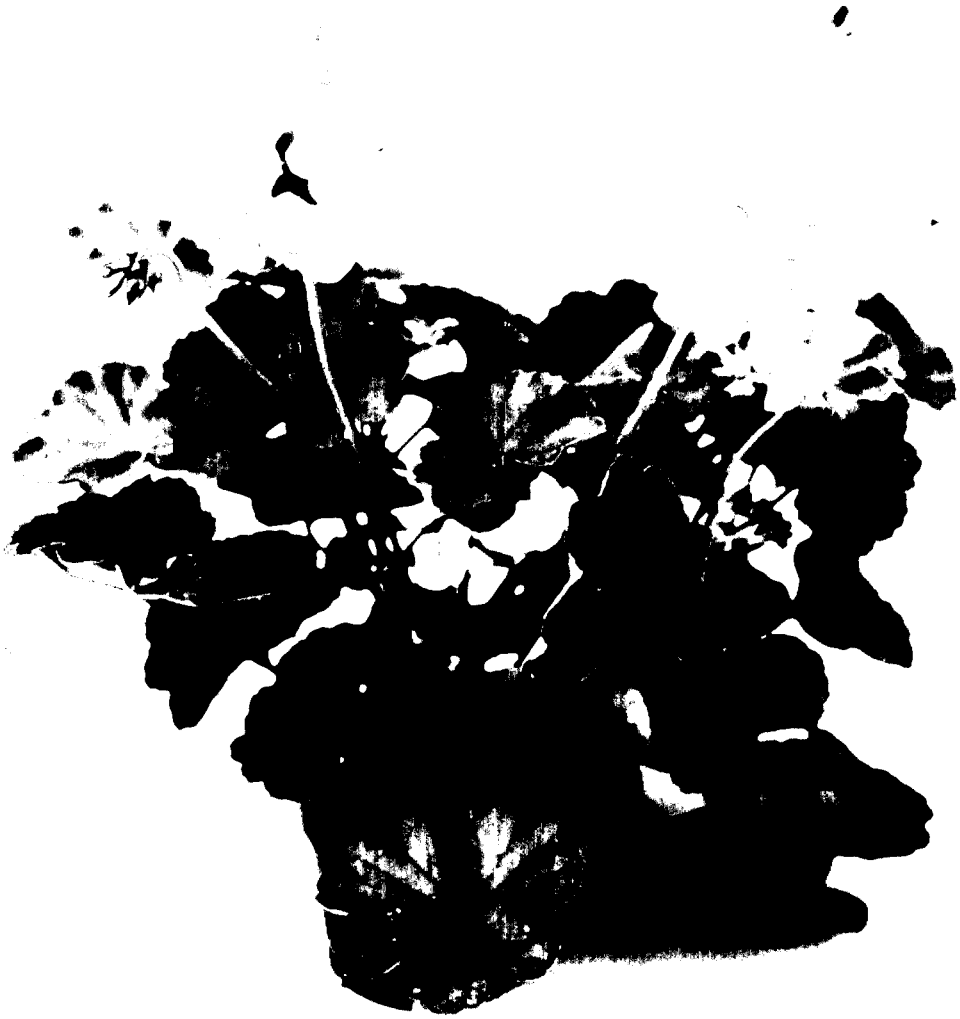

* * * * *